United States Patent [19]

Dor

[11] 4,043,903
[45] Aug. 23, 1977

[54] PROCESS FOR PROMOTION OF ALGAE GROWTH IN A SEWAGE MEDIUM

[76] Inventor: Inka Dor, 119 Ein Kerem D, Jerusalem, Israel

[21] Appl. No.: 626,292

[22] Filed: Oct. 28, 1975

[30] Foreign Application Priority Data

Nov. 8, 1974 Israel .................................. 46022

[51] Int. Cl.² .................... B01D 13/00; C02C 1/04
[52] U.S. Cl. ................................ 210/22 C; 47/1.4; 210/11
[58] Field of Search ............... 47/1.4; 210/11, 22, 210/23 F, 321 R, 321 A, 321 B, 500 M

[56] References Cited

U.S. PATENT DOCUMENTS

| 70,317 | 10/1867 | Brackett et al. | 210/22 |
|---|---|---|---|
| 2,692,854 | 10/1954 | Henley | 210/22 X |
| 3,218,758 | 11/1965 | Konikoff | 47/1.4 |
| 3,228,877 | 1/1966 | Mahon | 210/22 |
| 3,444,647 | 5/1969 | Takahashi | 210/11 X |
| 3,521,400 | 7/1970 | Ort | 210/11 X |
| 3,562,152 | 2/1971 | Davison | 210/22 |
| 3,598,726 | 8/1971 | Welch | 210/11 X |
| 3,856,569 | 12/1974 | Strong | 210/23 F |

OTHER PUBLICATIONS

Dempewolff, "Gardens to Feed Our Spacemen," 6/1960, Popular Mechanics, vol. 113, No. 6, pp. 123-127, 194, 195, 236-242.

*Primary Examiner*—Thomas G. Wyse
*Assistant Examiner*—Robert H. Spitzer
*Attorney, Agent, or Firm*—Holman & Stern

[57] ABSTRACT

An improved method for promoting algae growth in a sewage medium is disclosed. A high density algae culture can be obtained in a sewage water treatment process by placing algae in pure water separated by a dialysis membrane from sewage water wherein osmotic interaction occurs across the membrane. In a preferred embodiment algae is placed in pure water in dialysis tubing and the tubing is suspended in the presence of light in sewage water for osmotic interaction therewith.

2 Claims, 6 Drawing Figures

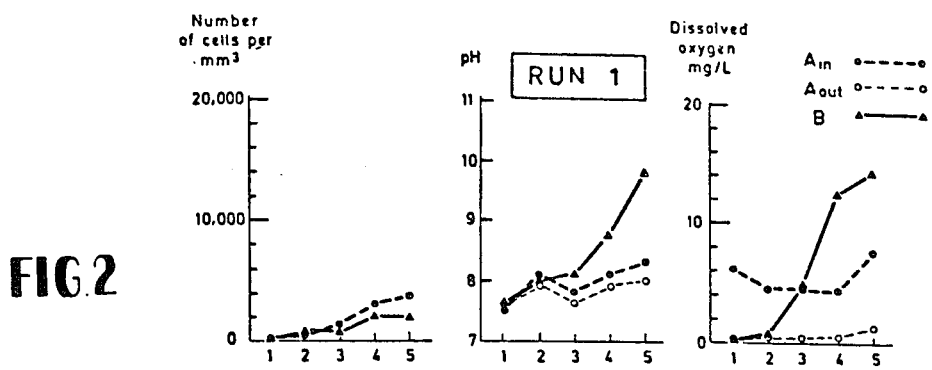
FIG.2
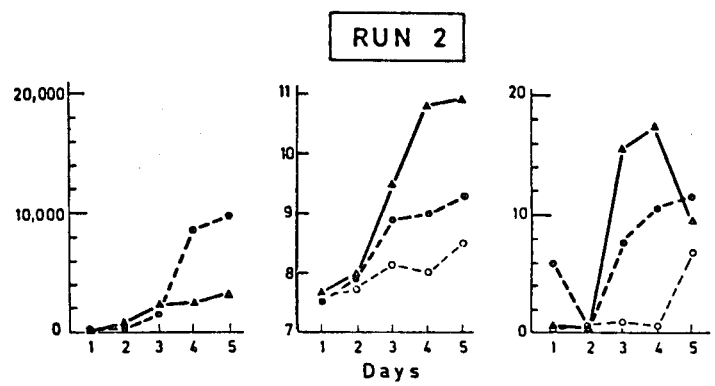
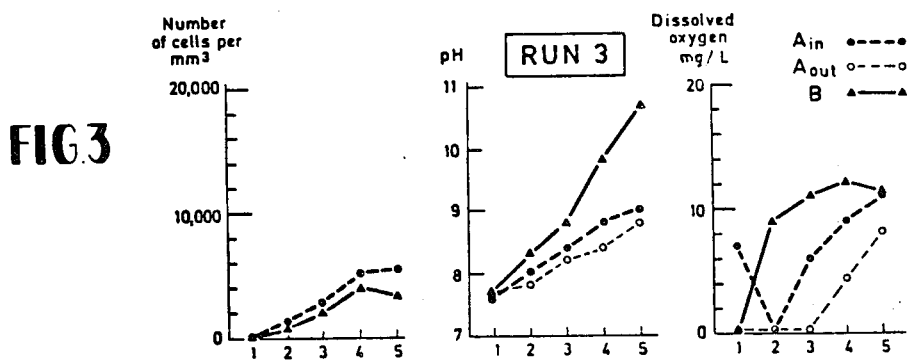
FIG.3
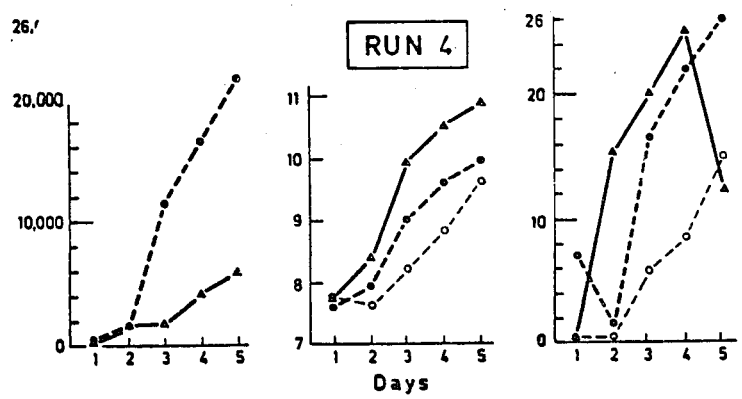

PROCESS FOR PROMOTION OF ALGAE GROWTH IN A SEWAGE MEDIUM

The present invention relates to an improved method for promoting algae growth in a sewage medium.

Many recent publications including Humenik and Hanna, *Journal Water Poll. Control Fed.* 43,580–594(1971), Goldman et al. *Occasional Paper* 6, pp 56 Utah State Univ. (1971) and Foree and Scorggin *J. Env. Eng. Div.* 99, No. EES, 639–652 (1973) have paid special attention to the biological and technological aspects of algal growth on sewage with not only plays a central role in the photosynthetic oxygenation of waste waters but also promotes the production of an algal biomass rich in proteins having nutritional value.

In said prior art processes waste sewage water was emptied into large catch basins and algae added to the basin. It was found that the waste matter supplied $CO_2$, bacteria and nutrients condusive to the growth of the algae while the algae during photosynthesis produced oxygen which oxygenated said waste materials and resulted in its purification. The algae was then removed strained and processed as a possible source of protein for animal feed.

One of the technological obstacles in the exploitation of the single-cell algae produced for food production is the necessity of their separation from the culture-suspension which is a rather expensive procedure accounting for 60% of production cost and involving such techniques as centrifugation, flocculation, reverse osmosis, etc. Additionally an algal biomass grown on sewage is contaminated with the enteric micro-organisms, which limits its use as food.

It has now been discovered according to the present invention that a high density algae culture could be produced in sewage water treatment processes by placing algae in pure water separated by a dialysis membrane from sewage water wherein osmotic interaction occurs across said membrane.

In a preferred embodiment of the present invention algae is placed in pure water in dialysis tubing and said tubing is suspended in the presence of light in sewage water for osmotic interaction therewith.

The osmotic exchange that takes place between the algal culture and the voluminous surrounding bacterial culture considerably intensifies algal growth and enables production of an unusually concentrated biomass. This biomass extracts nutrients from the waste water through the semipermeable dialysis-wall but remains separated from the suspended solids, bacteria and viruses of the raw sewage.

Thus while the prior art refers to production of 0.5–0.8 gm/liter of algae the present method produces in the same time interval, 3–4 gm per liter. Furthermore the use of dialysis tubing having a membrane porosity size smaller than virus diameter assures that no bacteria or viruses can contaminate the biomass. Consequently, after the growth period, the dialysis tubing with the clean and concentrated algal biomass is removed from the sewage avoiding processes of separation of the algae from the medium.

Dialysis culturing of microorganisms has been practiced for years, particularly to obtain a concentrated biomass. A paper published by Shultz and Gerhardt in *Bacterial Rev.* 33 p 1–47 (1969) describes the basic design, theory and various applications of dialysis culturing. Recently this technique was successfully used for the study of marine phytoplankton and for monitoring the nutritional capacity of sea water, however none of said references teach or suggest the use of dialysis culturing for growing algae on sewage for food production or the surprisingly high density of algae and ratio of chlorophyl to dry weight algae obtainable thereby.

BRIEF DESCRIPTION OF THE DRAWINGS

In order that the invention may be understood more fully, reference should be had to the following illustrative description read in conjunction with the accompanying figures, in which:

FIG. 2 to 6 are graphical charts of experimental results.

DESCRIPTION OF THE PREFERRED EMBODIMENTS

Figure 1:
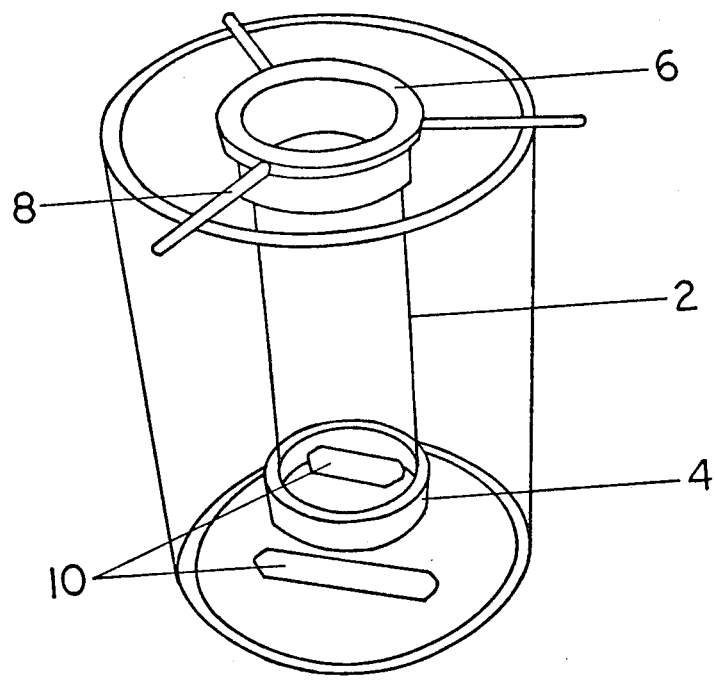
FIG. 1 is front perspective view of a growth unit used in the examples hereinafter.

Referring now to FIG. 1 there is illustrated dialysis tubing 2 closed at the bottom with a Petri dish cover and fastened with a metal ring 4. The top of the tubing is stretched over a second ring 6 and is tied to it. A simple frame made of soft wire 8 supports the suspended tubing. The inner algal phase and the outer bacterial phase are stirred with magnetic bars 10 by means of a stirrer (not shown).

While the invention will now be described in connection with certain preferred embodiments in the following illustrative Figures and examples it will be understood that it is not intended to limit to invention to these particular embodiments. On the contrary it is intended to cover all alternatives, modifications and equivalents as may be included within the scope of the invention as defined by the appended claims.

EXAMPLE 1

300 ml of tap water were inoculated with *Scenedesmus obliquus,* the naturally dominating strain of algae in our local oxidation ponds, placed in dialysis regenerated cellulose tubing having a diameter of 84 mm and a porosity of 24 angstrom units (obtained from Arnold, R. Horwell, London) and suspended in an 1800 ml, open beaker filled with raw sewage. Conventional mixed cultures were inoculated directly on sewage and grown in a similar beaker. The initial concentration of algae in the mixed cultures and inside dialysis tubing was 100–200 cells/mm³. This was obtained by the addition of about 7% of the stock culture to the culture medium. The stock culture was maintained on raw, domestic sewage of Jerusalem,. (Average composition BOD=500 mg/l, COD=900 mg/l, $N_k$ = 60 mg/l). The cultures were incubated in a thermostatic bath in 30° C, under continuous illumination of white fluorescent light supplemented by a tungstan lamp. Experiments were conducted at two light intensities: runs 1 and 3 at 6,000 lux and runs 2 and 4 at 22,000 lux.

Cell number and changes of pH and dissolved oxygen were measured daily. Results are given in FIGS. 1 and 2. The two runs in a given figure were carried out simultaeoulsy with the sewage sampled at the same time and inoculated identically and are therefore directly comparable. However, comparison between the two figures can be made with some reservation taking into account fluctuations in the composition of the sewage.

The results of the above example will now be discussed with reference to FIGS. 2 and 3 in which:

FIG. 2 shows in graphical form curves of growth, pH and dissolved oxygen in batch cultures of Scenedesmus grown in dialysis tubing suspended in sewage (A-in = algal phase and A-Out = bacterial phase) and in the conventional, mixed culture (B); and FIG. 3 shows in graphical form curves of growth, pH and dissolved oxygen in batch cultures of Scendesmus grown in dialysis tubing suspended in sewage and in the conventional mixed culture.

In all runs algal growth was more intensive in cultures A than in cultures B but the final difference between cell concentrations was much greater in runs No. 2 and 4, carried out under illumination of 22,000 lux, than in runs No. 1 and 3 grown under 6,000 lux.

The conventional, mixed cultures reached similar final cell concentrations under low and high light intensities, pointing to nutrient or other medium limitation. Dialysis cultures under low light were only slightly stimulated by the presence of the surrounding bacterial medium, indicating light limitation.

Significant stimulation took place only in the presence of both: osmotic contact with the sewage and strong light. On the fifth day, cultures A, under strong light reached the density of 10,000 to 21,000 cells/mm$^3$ while cultures B reached only 3,000 to 6,000 cells/mm$^3$. Thus while it is to be noted that even the dialysis cultures under low light intensity surpassed the cell concentrations of the conventional mixed cultures higher light intensities (e.g. in a range of about 15,000-25,000 lux and higher result in superior results and are preferred.

The pH of A-in algal medium (FIG. 2 and 3) was consistently lower than those of B, indicating a more adequate $CO_2$ supply to the dialysed culture. The parallel pH changes in and out of the dialysis tubing indicate continuous, free exchange between the chambers. Of course the pH of the algal phase (A-in) was always higher that of the external, bacterial phase (A-out).

The changes in oxygen concentrations had a less regular course than those of pH. Dissolved oxygen content (DO) was usually higher in B than in A but in the experiments with strong light A- cultures had on the last day more oxygen than cultures B. Oxygen concentrations were naturally higher in the A-in algal phase, where it was produced, than in A-out bacterial phase. The change in oxygen concentrations seen in the two media indicate its exchange across the dialysis membrane. Further evidence of such an exchange is the proliferation of the algal cultures in A-in, which were inoculated on tap water and thus totally dependent for nutrient supply on diffusing materials from A-out.

In these experiments the algal phase of the dialysis cultures contained from the beginning an inoculum of the heterotrophic bacteria present in the stock culture of Scenedesmus on sewage. These bacteria developed abundantly on the soluble organic matter diffusing from the surrounding sewage. However, the small porosity of dialysis membranes prevents passage of the enteric bacteria and viruses. While membranes having a porosity of 24 A were used, since viruses have a diameter of about 300 angstrom units the membrane porosity size can in fact be much larger, e.g. up to about 250A which size can even improve diffusion in the system with further stimulation of algal growth.

The yields reached on the fifth day in the conventional and dialysed cultures of Scenedesmus on sewage described in Example 1 were calculated and the minimum mean of five experiments were compared as was the mean of five experiments carried out in accordance with example 1 with dialysis tubing having a diameter of 44 mm.

The results of said comparison are given in the following Table:

Table 1

|  | No. Cells/mm$^3$ | Dry weight g/L | chlorophyll a mg/L |
|---|---|---|---|
| B (conventional) | 3,500 | 0.8 | 5 |
| A$_8$ (84 mm dialysis) | 13,000 | 1.8 | 32 |
| A$_4$ (40 mm dialysis tube) | 36,000 | 3,0 | 53 |

From the above table it can be seen that dialysis cultures yield not only higher concentration of biomass but all result in a marked increase in chlorophyll a content per unit dry weight.

Since chlorophyll content is usually corellated with protein content, it is asumed that dialysed cultures are also comparatively richer in proteins.

The above results demonstrate the possiblity of obtaining higher concentrated algal culture grown on sewage but not mixed with it and makes this method particularly suitable for production of single-cell algal protein from waste waters.

Furthermore it can be seen that a decrease in diameter of the dialysis tubing results in an increase in yields and thus it is envisioned that in actual production conditions narrow dialysis tubing well be distributed in a waste basin e.g. in a series of rows for maximum surface contact and yields, although it is also possible to have the sewage water flow through dialysis tubing distributed in a basin containing pure water and algae.

Additional experiments were also carried out to determine if the process of the present invention also presented advantages with regard to the purification of the sewage and thus the hereinafter described experiment was conducted to examine the influence of algae on bacterial growth on sewage by comparing bacterial activity in three kinds of media:

1. Stirred sewage incubated without algae (S)
2. Algal-bacterial culture on sewage (B)
3. Sewage medium in which was suspended in a dialysis bag with the culture of Scenedesmus (A).

EXAMPLE 2

Culture A and B were prepared as in example 1 and culture S was used for comparison. The cultures were incubated in 2 liters beakers in a theromostatic bath at 25° C, under continuous illumination of 22,000 lux. The cultures were stirred with magnetic bars on stirrers. At the start of experiments concentration of algalcells in the mixed culture B and in the dialysis-bag culture A was about 300 cells / mm$^3$.

Experiments lasted four days. Bacterial activity was examined in three different ways: a) growth was determined by daily counting bacterial colonies on nutrient agar plates; b) respiration of the cultures was measured as a rate of oxygen consumption; and c) BOD removal was used as an indirect measure of bacterial decomposition.

The cultures were sampled a few times on the first day and once per day during the next days of experiment. The samples were innoculated on nutrient agar. After incubation for 24 hr. at 30° C colonies on the plates were counted.

Simultaneously rate of oxygen consumption of the cultures was measured according to Humenik and Hanna (1972). Before starting respiration measurements, the sample was vigorously stirred, until oxygen concentration reached 6-7 ppm. Then the sample was placed in a 100 ml erlenmeyer flask, stopped hermetically with the oxygen electrode connected with an YSI Model 54 Oxygen Meter, placed in a thermostatic bath at 25° C and stirred in darkness. Dissolved oxygen decline was recorded at three to five minute intervalls. All measurements were conducted within the range of 3-7 ppm DO. Mean of 3-4 consecutive readings was taken as a rate of oxygen consumption at the given time. DO and pH of the cultures were measured regularly at the time of each sampling.

BOD of the medium-filtrate was examined on the beginning and at the end of each run, according to Standard Methods (1972).

Figure 4:
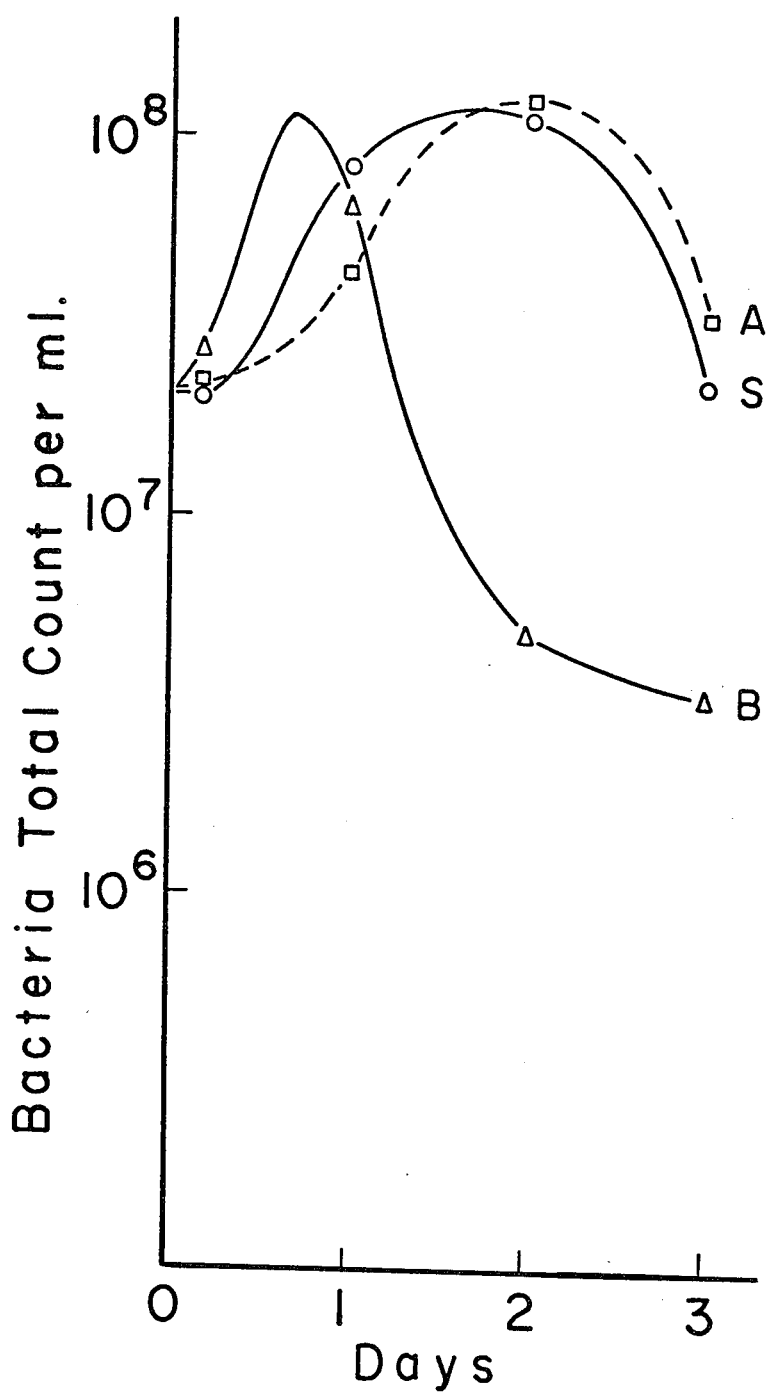

Bacterial counts on the nutrient agar plates as shown in FIG. 4 showed that the bacteria in the sewage mixed with algae (B) had different course of growth than in the both other cultures (A and S).

In culture B an increase in bacteria numbers started early after inoculation of the algae, continued for the next 12-18 hr and was followed by a slopy drop. In both other cultures (A and S) the increase in bacteria numbers was slower but continued for a longer time and the peak was reached after 40 (—60) hr. The following decline was gradual. On the second day of experiments the mixed B culture had about hundred times less bacteria than the A and S cultures. On the last day, with decline of bacterial counts in A and S these cultures still had more bacteria by a factor of ten than the culture mixed with algae.

Figure 5:
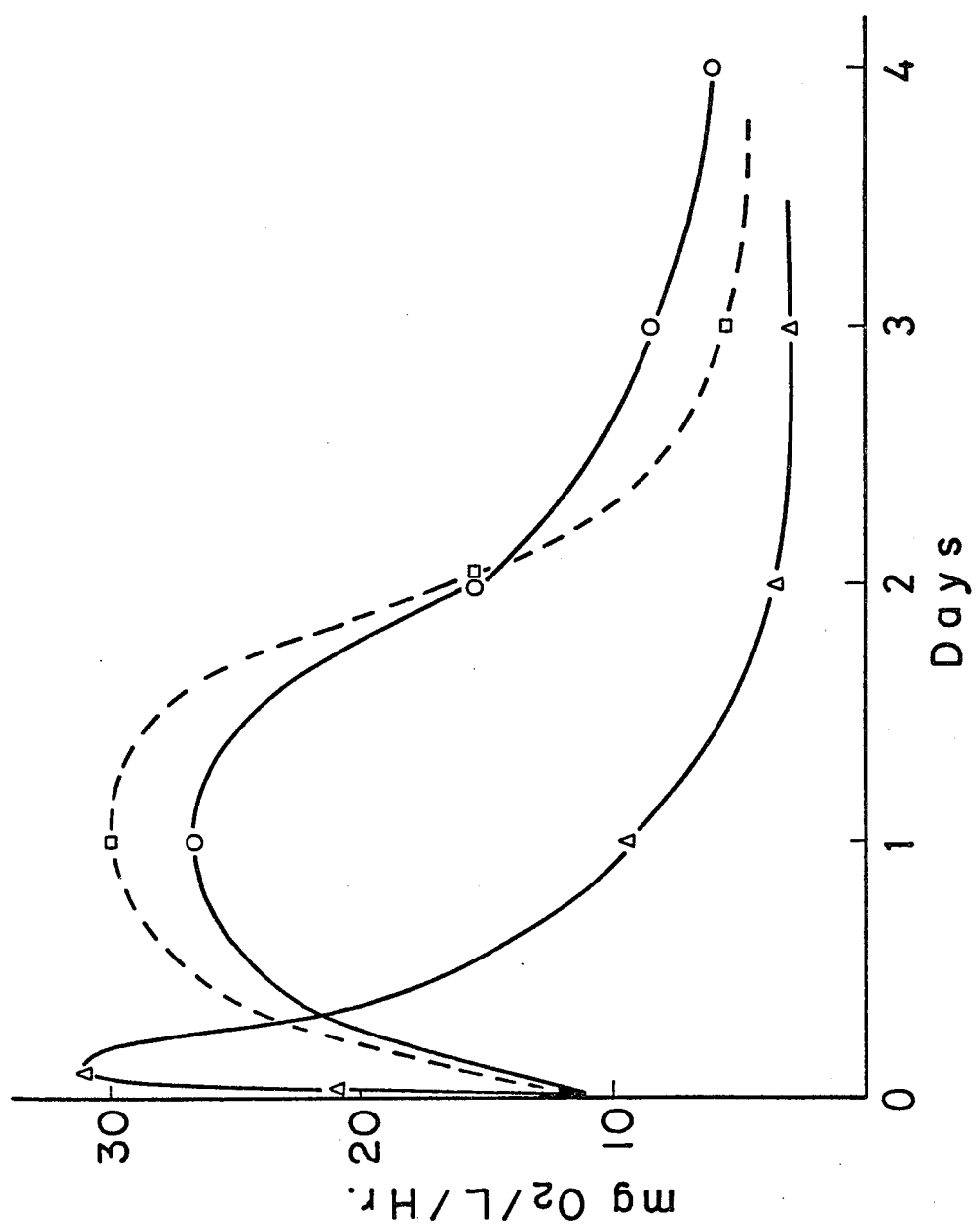

Rate of Oxygen consumption as shown in FIG. 5 in the presence of algae showed a sudden increase, which started a few minutes after algae were added to the sewage. The peak in consumption rate was reached after 2 hours and was followed by a steep decline. In the same time the two other cultures showed a slower, gardual increase in the rate of oxygen consumption, which continued about 24 hr. The peak reached by the sewage medium of the dialysed culture A was generally higher than the peak in the sewage S. The following decline in cultures A and S was gradual. On the last day of experiments the rate of oxygen consumption in both these cultures was still considerably higher than in the algal culture B.

The pH and dissolved oxygen in culture B showed a steep increase during the first day and remained high during the remaining days of experiment. However, in the first 6 hours, during which an increase and a decline of bacterial activity occured, DO concentration changed only from 1.2 to 2.2ppm and pH from 7.1 to 7.8. In the sewage medium of the culture A considerable increase in DO and pH occurred on the third day. This change was induced by the algal culture developing inside dialysis bag. In culture S the pH and DO remained almost unchanged during the 3 days of experiments.

Figure 6:
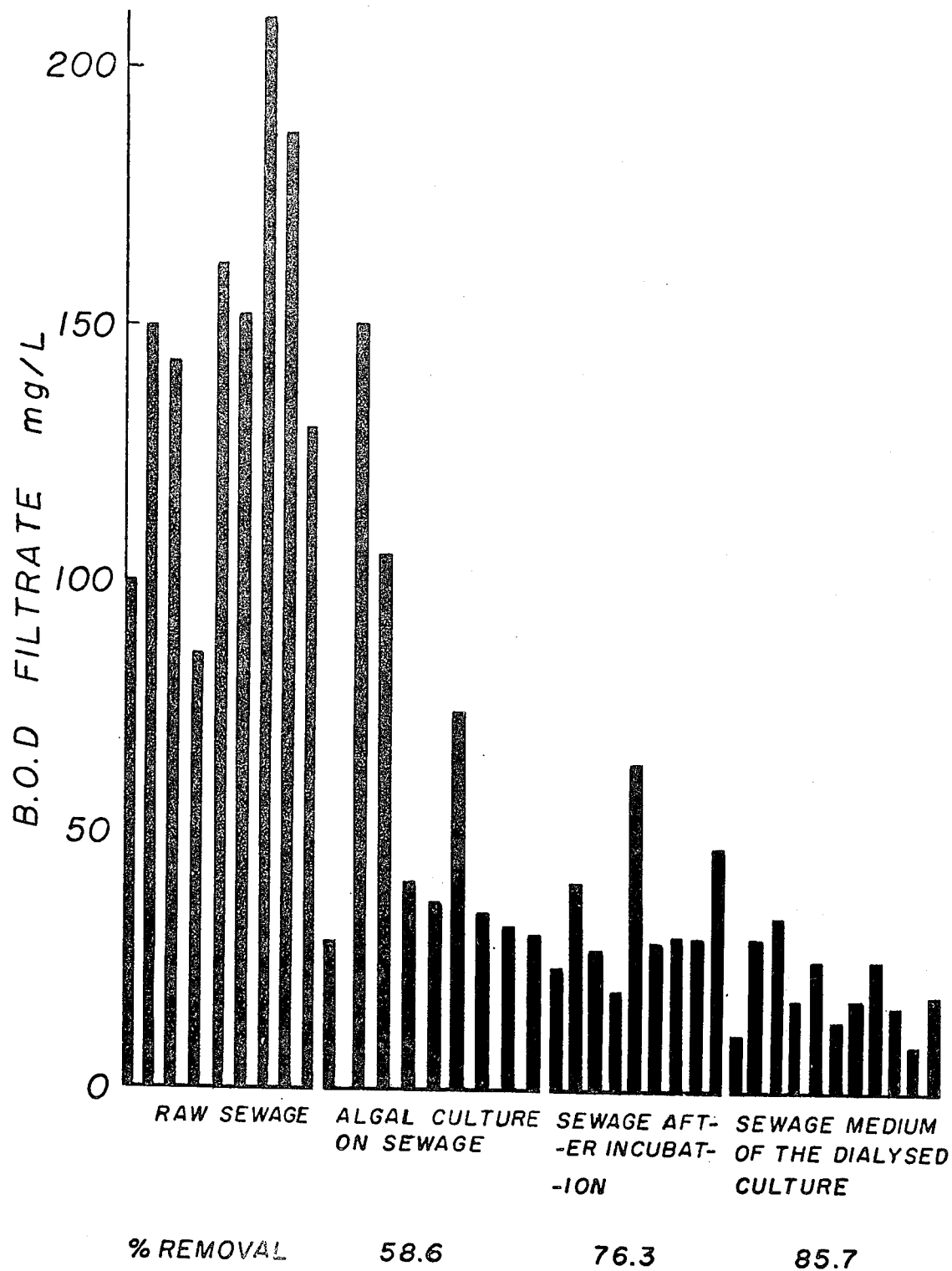

Removal of the BOD after four days of the incubation was 85% in A, 76% in S and only 58% in B in the presence of algae as shown in FIG. 6 and the difference between the results in A and B is especially surprising in light of the fact that thhe prior art has heretofor used the culture represented by B for photosynthetic oxygenation of waste waters.

In the sewage mixed with algae (B), the bacterial population, which is able to grow on nutrient agar in aerobic conditions at 30° C — showed an early decline and low numbers during the remaining time of incubation. Accordingly the efficiency of BOD removal in this culture was substantially lower as compared with other cultures. Evidently the same bacteria, which grew on nutrient agar, were responsible for the decomposition for the decomposition of the organic load of the sewage.

Additional support for this view is supplied by respiration experiments. Oxygen consumption rate in culture B, after a sudden increase during first two hours, showed a sloping drop and remained low during the following days as compared with the respiration in both other cultures A and S which were not mixed with algae. Final decline of the respiration in these last cultures probably occured when the amount of the decomposable organic matter became a limiting factor.

Correlation between results obtained from all three methods indicated by no means that bacteria responsible for decomposition of organic matter in sewage were inhibited in the presence of algae.

Algae may influence bacteria in several ways including by promoting changes in pH and DO and/or by excreting substances affecting bacterial growth.

DO and pH of the cultures did not change substantially during the first 6 hours of the experiments. Therefore, the differences in the number of bacteria and in the respiratory activity, which occurred in this time interval — must be related to the factor other than dissolved oxygen concentraton on pH.

One possible explanation for the results obtained is that an inhibitory substance excreted by Scenedesmus adversly affected bacterial activity. Lack of inhibition in the dialysed culture medium suggests, that the inhibiting factor has a high molecular weight and does not pass dialysis membrane.

Therefore, avoiding direct contact between bacteria and algae is beneficial for both organisms: bacteria separated from algae develop their full capacity in breakdown of organic matter — and algae on the other side are enriched with an increased flux of the mineralized nutrients diffusing through the semipermeable dialysis membrane. As a result water purification is accelerated while the concentrated algal biomass may be easily removed from the medium by simply taking out the dialysis bag and the use of the process of the present invention for water purification is also intended to be within the scope of the present invention.

It will be evident to those skilled in the art that the invention is not limited to the details of the foregoing illustrative embodiments and that the present invention may be embodied in other specific forms without departing from the spirit or essential attributes thereof. It is therefore desired that the present embodiments be considered in all respects as illustrative and not restrictive, reference being made to the appended claims, rather than to the foregoing description in which it is intended to claim all modifications coming within the scope and spirit of the invention.

What is claimed is:

1. An improved method for promoting algae growth in sewage medium comprising placing algae in pure water separated by a dialysis membrane from sewage water in the presence of light of an intensity of at least about 15,000 lux and allowing osmotic interaction to occur across said membrane as a result of the difference in concentration gradient, wherein said dialysis membrane has a porosity in the range of about 250A to 24A.

2. The improved method of promoting algae growth in sewage medium of claim 1, further comprising placing algae containing water in dialysis tubing and suspending said tubing in the presence of light in sewage water for osmotic interaction therewith.

* * * * *